United States Patent
Dottori et al.

(10) Patent No.: US 9,932,707 B2
(45) Date of Patent: Apr. 3, 2018

(54) BAGASSE FRACTIONATION FOR CELLULOSIC ETHANOL AND CHEMICAL PRODUCTION

(71) Applicant: GREENFIELD SPECIALTY ALCOHOLS INC., Toronto (CA)

(72) Inventors: Frank A. Dottori, Temiscaming (CA); Robert Ashley Cooper Benson, North Bay (CA); Régis-Olivier Benech, Chatham (CA)

(73) Assignee: GreenField Specialty Alcohols Inc., Toronto (CA)

( * ) Notice: Subject to any disclaimer, the term of this patent is extended or adjusted under 35 U.S.C. 154(b) by 88 days.

(21) Appl. No.: 14/940,992

(22) Filed: Nov. 13, 2015

(65) Prior Publication Data

US 2016/0069020 A1    Mar. 10, 2016

Related U.S. Application Data

(63) Continuation-in-part of application No. 13/289,358, filed on Nov. 4, 2011, now Pat. No. 9,187,862.

(Continued)

(51) Int. Cl.
*D21C 1/02* (2006.01)
*C08H 8/00* (2010.01)
(Continued)

(52) U.S. Cl.
CPC ............ *D21C 1/02* (2013.01); *C08B 37/0057* (2013.01); *C08H 8/00* (2013.01); *C13K 1/02* (2013.01);
(Continued)

(58) Field of Classification Search
USPC .......................................................... 162/68
See application file for complete search history.

(56) References Cited

U.S. PATENT DOCUMENTS 4,136,207 A    1/1979  Bender
4,409,032 A    10/1983 Paszner
(Continued)

FOREIGN PATENT DOCUMENTS

CA    2368872    10/2000
CA    2477196    8/2003
(Continued)

OTHER PUBLICATIONS

Shapouri et al., "Estimating the net energy balance of corn ethanol; An Economic Research Service Report", USDA Report 721, Jul. 1995, 13 pages.

(Continued)

*Primary Examiner* — Jacob Thomas Minskey
(74) *Attorney, Agent, or Firm* — Borden Ladner Gervais LLP (57) ABSTRACT

A process is defined for the continuous steam pretreatment and fractionation of bagasse to produce a concentrated cellulose solid stream that is sensitive to enzymatic hydrolysis. Valuable chemicals are recovered by fractionating the liquid and vapor stream composed of hydrolysis and degradation products of the hemicellulose. Cellulosic derived glucose is produced for fermentation to biofuels. A hemicellulose concentrate is recovered that can be converted to value added products including ethanol.

17 Claims, 3 Drawing Sheets

Related U.S. Application Data (60) Provisional application No. 61/410,701, filed on Nov. 5, 2010.

(51) Int. Cl.
| | | |
|---|---|---|
| *C13K 1/02* | (2006.01) | |
| *C13K 13/00* | (2006.01) | |
| *D21C 11/00* | (2006.01) | |
| *D21H 11/12* | (2006.01) | |
| *C08B 37/00* | (2006.01) | |
| *C12P 19/02* | (2006.01) | |
| *C12P 19/14* | (2006.01) | |
| *C12P 7/10* | (2006.01) | |

(52) U.S. Cl.
CPC ........ *C13K 13/002* (2013.01); *D21C 11/0007* (2013.01); *D21H 11/12* (2013.01); *C12P 7/10* (2013.01); *C12P 19/02* (2013.01); *C12P 19/14* (2013.01); *C12P 2201/00* (2013.01)

(56) References Cited

U.S. PATENT DOCUMENTS

| | | | |
|---|---|---|---|
| 4,461,648 A * | 7/1984 | Foody | 127/37 |
| 4,470,851 A | 9/1984 | Paszner | |
| 4,764,596 A | 8/1988 | Lora | |
| 4,966,650 A | 10/1990 | De Long | |
| 5,730,837 A | 3/1998 | Black | |
| 7,368,037 B2 | 5/2008 | Vaders | |
| 2002/0069987 A1 | 6/2002 | Pye | |
| 2002/0148575 A1 | 10/2002 | Wingerson | |
| 2003/0041982 A1 | 3/2003 | Prior | |
| 2005/0161038 A1 | 7/2005 | Pinatti et al. | |
| 2007/0034345 A1 | 2/2007 | Petrus | |
| 2007/0259412 A1 | 11/2007 | Belanger | |
| 2008/0032344 A1 | 2/2008 | Fallavollita | |
| 2008/0196847 A1 | 8/2008 | Van Heiningen et al. | |
| 2010/0263814 A1 | 10/2010 | Dottori et al. | |
| 2010/0269990 A1 | 10/2010 | Dottori et al. | |
| 2010/0313882 A1 | 12/2010 | Dottori et al. | |
| 2011/0065785 A1* | 3/2011 | Larsen | 514/461 |
| 2013/0014729 A1 | 1/2013 | Saito et al. | |
| 2013/0017589 A1 | 1/2013 | Dottori et al. | |
| 2013/0029406 A1 | 1/2013 | Dottori et al. | |

FOREIGN PATENT DOCUMENTS

| | | |
|---|---|---|
| CA | 2595484 | 2/2008 |
| CA | 2701194 | 10/2010 |
| CA | 2701407 | 10/2010 |
| DE | 19730486 | 1/1999 |
| WO | 1993/15261 | 8/1993 |
| WO | 1997/36040 | 10/1997 |
| WO | 2007/009463 | 1/2007 |
| WO | 2009/031164 | 3/2009 |
| WO | 2009/108773 | 9/2009 |
| WO | 2009116070 | 9/2009 |

OTHER PUBLICATIONS

Shapouri et al., "The Energy Balance of corn ethanol: an update", USDA Report 814, Jul. 2002, 19 pages.
Wald et al., "The Energy challenge: A Renewed push for ethanol, without the corn", New York Times, Apr. 17, 2007, 5 pages.
Greer, "Commercializing cellulosic ethanol", Biocycle, vol. 49, Nov. 2008, No. 11, 4 pages.
Hill et al. "Environmental, economic, and energetic costs and benefits of biodiesel and ethanol biofuels", Proc. Natl. Acad. Sci. USA, Jul. 25, 2006, vol. 103, No. 30, pp. 11206-11210.
Farrell et al., "Ethanol can contribute to energy and environmental goals", Science, Jan. 27, 2006, vol. 311, 23 pages.
Somerville, "Biofuels", Current biology, 2007, vol. 17, No. 4, pp. 115-119.
Schuetzle et al., "Alcohol fuels from biomass—Assessment of production technologies", Western Governors' Association National Biomass and Regional Partnership Report, Jul. 2007, pp. 1-119, (125 pages).
Neely, "Factors affecting the pretreatment of biomass with gaseous ozone", Biotechnology and Bioengineering, vol. XXVI, Jan. 1984, pp. 59-65.
Vidal et al., "Improvement of in vitro digestibility of poplar sawdust", Biomass, 1988, vol. 16, pp. 1-17.
Delmer et al., "Cellulose biosynthesis", American Society of Plant Physiologist, The Plant Cell, vol. 7, Jul. 1995, pp. 987-1000.
Morohoshi, "Chemical characterization of wood and its components", In Wood and cellulosic chemistry; Hon, D.N.S, Shiraishi, N., Eds.; Marcel Dekker, Inc.: New York, USA, 1991, pp. 331-392.
de Vrije et al, "Pretreatment of Miscanthus for Hydrogen Production by Thermotoga Elfii", International Journal of Hydrogen Energy, Nov.-Dec. 2002, vol. 27, pp. 1381-1390.
Ha et al., "Fine Structure in cellulose microfibrils: NMR evidence from onion and quince", The Plant Journal, Aug. 27, 1998, published 1998, vol. 16, No. 2, pp. 183-190.
Palmqvist et al., "Fermentation of lignocellulosic hydrolysates. II: Inhibitors and mechanisms of inhibition", Bioresource Technology, Aug. 2000, vol. 74, pp. 25-33.
Galbe et al., "A review of the production of ethanol from softwood", Appl Microbial Biotechnol, vol. 59, published online Jul. 17, 2002, pp. 618-628.
Torget et al., "Dilute sulfuric acid pretreatment of hardwood bark", Bioresource Technology, vol. 35, 1991, pp. 239-246.
Donghai et al., "Effects of different pretreatment modes on the enzymatic digestibility of corn leaf and corn stalk", Chinese Journal of Eng., vol. 14, No. 6, 2006, pp. 796-801.
Sun et al., "Hydrolysis of lignocellulosic materials for ethanol production: A review", Bioresource Technology, vol. 83, 2002, pp. 1-11.
McMillan et al., "Pretreatment of lignocellulosic biomass", Biprocessing Branch, Alternative Fuels Division, National Renewable Energy Laboratory, 1994, American Chemical Society, pp. 292-324.
Fan et al., "The nature of lignocellulosics and their pretreatments for enzymatic hydrolysis", Advances in Biochemical Engineering, 1982 vol. 23, pp. 158-187.
Mosier et al., "Features of promising technologies for pretreatment of lignocellulosic biomass", Bioresource Technology, vol. 96, available online Sep. 29, 2004, pp. 673-686.
Henley et al., "Enzymatic saccharification of cellulose in membrane reactors", Enzyme Microb. Tech., vol. 2, Jul. 1980, pp. 206-208.
Berlin et al., "Inhibition of cellulase, xylanase and beta-glucosidase activities by softwood lignin preparations", Journal of Biotechnology, vol. 125, Sep. 1, 2006, pp. 198-209.
Chandra et al. "Substrate pretreatment: The key to effective enzymatic hydrolysis of lignocellulosics?", Adv. Biochem Engin/Biotechnol., published online May 26, 2007, vol. 108, pp. 67-93.
Kassim, "Enzymatic and chemical hydrolysis of certain cellulosic materials", Agricultural Wastes, vol. 17, 1986, pp. 229-233.
Xu et al., "Enzymatic hydrolysis of pretreated soybean straw", Biomass and Bioenergy, vol. 31, Feb. 2007, pp. 162-167.
Vaccarino et al., "Effect of SO2NaOH and Na2CO3 pretreatments on the degradability and cellulase digestibility of grape Marc", Biological Wastes, vol. 20, 1987, pp. 79-88.
Silverstein et al., "A comparison of chemical pretreatment methods for improving saccharification of cotton stalks", Bioresource Technology, available online Dec. 8, 2006, No. 98, pp. 3000-3011.
Zhao et al., "Comparative study on chemical pretreatment methods for improving enzymatic digestibility of crofton weed stem", Bioresource Technology, available online Aug. 20, 2007, vol. 99, pp. 3729-3736.
Gaspar et al., "Corn fiber as a raw material for hemicellulose and ethanol production", Process Biochemistry, 2007, vol. 42, pp. 1135-1139.

(56) References Cited

OTHER PUBLICATIONS

Saha et al., "Ethanol production from alkaline peroxide pretreated enzymatically saccharified wheat straw", Biotechnol. Prog., published online Jan. 19, 2006, vol. 22, pp. 449-453.
Saha et al., "Enzymatic saccharification and fermentation of alkaline peroxide pretreated rice hulls to ethanol", Enzyme and Microbial Technology, vol. 41, 2007, pp. 528-532.
Mishima et al., "Comparative study on chemical pretreatments to accelerate enzymatic hydrolysis of aquatic macrophyte biomass used in water purification processes.", Bioresource Technology, available online Nov. 23, 2005, vol. 97, pp. 2166-2172.
Sun et al., "Characteristics of degraded cellulose obtained from steam-exploded wheat straw", Carbohydrate Research, available online Dec. 2, 2004, vol. 340, pp. 97-106.
Chum et al., "Evaluation of pretreatments of biomass for enzymatic hydrolysis of cellulose", Solar Energy Research Institute: Golden, Colorado, Oct. 1985, pp. 1-67.
Taherzadeh et al., "Acid-based hydrolysis processes for ethanol from lignocellulosic materials: A review", Bioresources, 2007, vol. 2, No. 3, pp. 472-499.
Ruiz et al., "Evaluation of steam explosion pre-treatment for enzymatic hydrolysis of sunflower stalks", Enzyme and Microbial Technology, vol. 42, Jan. 2008, pp. 160-166.
Ballesteros et al., "Ethanol from lignocellulosic materials by a simultaneous saccharification and fermentation process (SFS) with Kluyveromyces marxianus CECT 10875", Process Biochemistry, vol. 39, 2004, pp. 1843-1848.
Negro et al., "Hydrothermal pretreatment conditions to enhance ethanol production from poplar biomass", Applied Biochemistry and Biotechnology, vol. 105-108, Mar. 2003, pp. 87-100.
Kurabi et al., "Enzymatic hydrolysis of steam exploded and ethanol organosolv-pretreated Douglas-fir by novel and commercial fungal cellulases", Applied Biochemistry and Biotechnology, vol. 121-124, Mar. 2005, pp. 219-230.
Varga et al., "Optimization of steam pretreatment for corn stover to enhance enzymatic digestibility", Applied Biochemistry and Biotechnology, 2004, 42 pages.
Eklund et al., "The influence of SO2 and H2SO4 impregnation of willow prior to steam pretreatment", Bioresource Engineering, vol. 52, 1995, pp. 225-229.
Yang et al., "Effect of xylan and lignin removal by batch and flowthrough pretreatment on the enzymatic digestibility of corn stover cellulose", Biotechnol. Bioeng, Apr. 5, 2004, published online Feb. 13, 2004, vol. 86, pp. 88-95.
Alizadeh et al., "Pretreatment of switchgrass by ammonia fiber explosion (AFEX)", Applied Biochemistry and Biotechnology, vol. 121-124, Mar. 2005, pp. 1133-1141.
Chundawat et al., "Effect of particle size based separation of milled corn stover on AFEX pretreatment and enzymatic digestibility", Biotechnology and Bioengineering, vol. 96, No. 2, Feb. 1, 2007, pp. 219-231.
Eggeman et al., "Process and economic analysis of pretreatment technologies", Bioresource Technology, vol. 96, available online Mar. 10, 2005, pp. 2019-2025.
Taherzadeh et al., "Enzyme-based hydrolysis processes for ethanol from lignocellulosic materials: A review", BioResources, 2007, vol. 2, No. 4, pp. 707-738.
Azzam, "Pretreatment of cane bagasse with alkaline hydrogen peroxide for enzymatic hydrolysis of cellulose and ethanol fermentation", Journal Environ. Sci. Health, 1989, vol. 24, pp. 421-433.
Katzen et al., "Use of cellulosic feedstocks for alcohol production, Use of Cellulosic Feedstocks for Alcohol Production", The Alcohols Textbook, Chapter 5, Nothingham University Press, 1959. pp. 37-46.

Araque et al., "Evaluation of organosolv pretreatment for the conversion of Pinus radiata D. Don to ethanol", Enzyme and Microbial Technology, vol. 43, Aug. 5, 2008, pp. 214-219.
Pan et al., "Bioconversion of hybrid poplar to ethanol and co-products using an organosolv fractionation process: optimization of process yields", Biotechnol. Bioeng, Aug. 5, 2006, published online Mar. 7, 2006, vol. 94, No. 5, pp. 851-861.
Arato et al., "The Lignol Approach to Biorefining of Woody Biomass to Produce Ethanol and Chemicals", Applied Biochemistry and Biotechnology, vol. 121-124, Mar. 2005, pp. 871-882.
Muurinen, "Organosolv pulping—A review and distillation study related to peroxyacid pulping", University of Oulu, Finland, http://herkules.oulu.fi/isbn9514256611/isbn9514256611.pdf, ISBN 951-42-5661-1, presented Jun. 30, 2000, 314 pages.
Yang et al., "Pretreatment: the key to unlocking low-cost cellulosic ethanol", Biofuels, Bioproducts and Biorefinering, Jan. 2008, published online Dec. 17, 2007, vol. 2, pp. 26-40.
International Application No. PCT/CA2010/000581, International Search Report dated Jul. 8, 2010.
Itoh et al., "Bioorganosolve pretreatments for simultaneous saccharification and fermentation of beech wood by ethanolysis and white rot fungi", Journal of Biotechnology, vol. 103, Aug. 15, 2003, pp. 273-280.
Chow et al., "Energy resources and global development", Science, vol. 302, Nov. 28, 2003, pp. 1528-1531.
Chum et al., "Biomass and renewable fuels.", (2002) Fuel Processing technology, 71, pp. 187-195.
Vazquez et al, "Enhancing the potential of oligosaccharides from corncob autohydrolysis as prebiotic food ingredients", Industrial Crops and Products, 24, 2006, pp. 152-159.
Moura et al., "In vitro fermentation of xylooligosaccharides from corncobs autohydrolysis by Bifidobacterium and Lactobacuillus strains", LWT, 40, 2007, pp. 963-972.
PCT/CA2011/050689 International Search Report dated Dec. 19, 2011.
European Patent Application No. 10766552.3 Extended European Search Report dated Sep. 26, 2012.
Australian Patent Application No. 2011325841, Examination Report dated May 20, 2015.
Columbian Patent Application No. 13-135299, English Translated Office Action dated Apr. 23, 2014.
Guillischsen editor, Chemical Pulping 6A/6B, Dec. 1999, Fapet Oy, p. A28-A29, A66, A577, and chapter 20.
Wyman, Handbook on Bioethanol: Production and Utilization, Jul. 1996, Taylor and Francis, United States of America, pp. 10-12.
Chum et al., "Biomass and Renewable Fuels", Fuel Processing Technology, Jun. 2001, vol. 71, Elsevier Science B. V., United States of America, pp. 187-195.
Nabarlatz et al., "Autohydrolysis of agricultural by-products for the production of xylo-oligasaccharides", Carbohydrate Polymers, Oct. 2006, vol. 69, Elsevier Science B.V., United States of America, pp. 20-28.
Chinese Patent Application No. 201180054719.8, Notice of Allowance dated Feb. 24, 2017, an English translation is not available.
Australian Patent Application No. 2011325841, Notice of Acceptance dated Dec. 21, 2015.
U.S. Appl. No. 13/289,358, Office Action dated Mar. 15, 2013.
U.S. Appl. No. 13/289,358, Office Action dated Sep. 18, 2013.
U.S. Appl. No. 13/289,358, Office Action dated Mar. 26, 2014.
U.S. Appl. No. 13/289,358, Office Action dated Dec. 24, 2014.
U.S. Appl. No. 13/289,358, Notice of Allowance dated Jul. 10, 2015.

\* cited by examiner

BAGASSE FRACTIONATION FOR CELLULOSIC ETHANOL AND CHEMICAL PRODUCTION

CROSS REFERENCE TO RELATED APPLICATIONS

The present application is a continuation-in-part of U.S. patent application Ser. No. 13/289,358 filed Nov. 4, 2011, which claims the benefit of priority of U.S. Provisional Patent Application No. 61/410,701 filed Nov. 5, 2010, the contents of which are incorporated herein by reference.

FIELD OF THE INVENTION

The present invention generally relates to the production of ethanol from lignocellulosic biomass and in particular to a process for extracting cellulose and hemicellulose from sugarcane bagasse.

BACKGROUND OF THE INVENTION

Concerns over high oil prices, security of supply and global warming have raised the demand for renewable energy. Renewable energy is energy produced from plant derived biomass. Renewable energy applications such as fuel ethanol are seen as a valuable contribution to the reduction in fossil fuel consumption. Public policies have supported the creation of a fuel ethanol industry largely based on the use of corn as a feedstock. The production of fuel ethanol helps to stabilize farm income and reduces farm subsidies. However, as demand increases for fuel ethanol, additional feedstocks such as lignocellulosic biomass are under consideration (1-3).

Fuel ethanol is created by the fermentation of starch derived sugars. The ethanol is distilled and dehydrated to create a high-octane, water-free gasoline substitute. Fuel ethanol is blended with gasoline to produce a hybrid fuel, which has environmental advantages when compared to gasoline alone, and can be used in gasoline-powered vehicles manufactured since the 1980's. Most gasoline-powered vehicles can run on a blend consisting of gasoline and up to 10 percent ethanol, known as "E-10" (4-10).

While corn is the major raw material for producing ethanol in North America, the dominant ethanol feedstock in warmer regions is sugarcane. It is already apparent that large-scale use of ethanol for fuel will require new technologies that will allow the industry to expand its feedstock options to include cellulose (4-10).

Cellulosic ethanol is manufactured from lignocellulosic biomass. Lignocellulosic biomass may be grouped into four main categories: (1) wood residues (including sawmill and paper mill discards), (2) municipal paper waste, (3) agricultural wastes (including corn stover, corn cobs and sugarcane bagasse), and (4) dedicated energy crops which are mostly composed of fast growing tall, woody grasses such as switch grass and *Miscanthus* (8-11).

Lignocellulosic biomass is composed of three primary polymers that make up plant cell walls: Cellulose, hemicellulose and lignin. Cellulose is a polymer of D-glucose. Hemicellulose contains two different polymers i.e. xylan, a polymer of xylose and glucomannan, a polymer of glucose and mannose. Lignin is a polymer of guaiacylpropane- and syringylpropane units (12-14).

Cellulose fibers are locked into a rigid structure of hemicellulose and lignin. Lignin and hemicelluloses form chemically linked complexes that bind water soluble hemicelluloses into a three dimensional array, cemented together by lignin. Lignin covers the cellulose microfibrils and protects them from enzymatic and chemical degradation. These polymers provide plant cell walls with strength and resistance to degradation, which makes lignocellulosic biomass a challenge to use as a substrate for biofuel production. Variation in the content or organization of these polymers significantly affects the overall steps of cellulosic ethanol production (12-14).

Cellulose or $\beta$-1-4-glucan is a linear polysaccharide polymer of glucose made of cellobiose units (12, 13). The cellulose chains are packed by hydrogen bonds in microfibrils (14). These fibrils are attached to each other by hemicelluloses, amorphous polymers of different sugars and covered by lignin.

Hemicellulose is a physical barrier which surrounds the cellulose fibers and protects cellulose against degradation. There is evidence that hemicellulose, containing xylose polymers (xylan), limits the activity of cellulolytic enzymes, thereby lowering cellulose to glucose conversion rates. (11-14). Thus for the production of fermentable sugars and ethanol, it is desirable to submit to the enzymatic hydrolysis a highly reactive cellulose low in xylan.

Lignin is a very complex molecule constructed of phenylpropane units linked in a three dimensional structure which is particularly difficult to biodegrade. Lignin is the most recalcitrant component of the plant cell wall. There are chemical bonds between lignin, hemicellulose and cellulose polymers. There is evidence that the higher the proportion of lignin, the higher the resistance to chemical and biological hydrolysis. Lignin and some soluble lignin derivatives inhibit enzymatic hydrolysis and fermentation processes (14, 15). Thus, it is desirable to use a lignocellulosic feedstock which is low in lignin.

The lignin content of bagasse is variable and ranges from low (10%) to high (25% by weight on a dry matter basis). The low lignin content of some bagasse residues makes this waste product a good biomass feedstock for the production of ethanol whereas high lignin bagasse is more suitable for cogeneration applications, in which bagasse is used as a fuel source to provide both heat energy, used in the mill, and electricity, which is typically sold on to the consumer electricity grid.

Published work on the various processes for the production of fermentable sugars from cellulosic biomass shows the existence of an inverse relationship between lignin content and the efficiency of enzymatic hydrolysis of sugar based polymers (16). Lignocellulosic microfibrils are associated in the form of macrofibrils. This complicated structure and the presence of lignin provides plant cell walls with strength and resistance to degradation, which also makes these materials a challenge to use as substrates for the production of biofuel and bioproducts. Thus, pretreatment is necessary to produce highly reactive cellulose that reacts well with catalysts such as enzymes (17).

Purified cellulose and lignin-free xylo-oligosaccharides are valuable for many purposes. Specifically, reactive cellulose extracted from biomass with low lignin content may be easily hydrolyzed to fermentable sugar monomers and then fermented to ethanol and other biofuels. Lignin-free xylo-oligosaccharides extracted from the hemicellulose fraction are valuable and may be easily used in the preparation of prebiotic substances for food and pharmaceutical applications.

The best method and conditions of pretreatment will vary and depend greatly on the type of lignocellulosic starting material used (18, 19). Pretreatment configuration and operating conditions must be adjusted with respect to the content or organization of lignocellulosic polymers in the starting material, to attain optimal conversion of cellulose to fermentable sugars (11). The cellulose-to-lignin ratio is the main factor. Other parameters to consider are the content of hemicellulose, degree of acetylation of hemicellulose, cellulose-accessible surface area, degree of polymerization and crystallinity (11).

An effective pretreatment should meet the following requirements: (a) production of reactive cellulosic fiber for enzymatic attack, (b) avoidance of cellulose and hemicelluloses destruction, and (c) avoidance of the formation of possible inhibitors for hydrolytic enzymes and fermenting microorganisms (17-20).

Several methods have been investigated for the pretreatment of lignocellulosic materials to produce reactive cellulose. These methods are classified into physical pretreatments, biological pretreatments and physicochemical pretreatments (21-22).

The prior art teaches that physical and biological pretreatments are not suitable for industrial applications. Physical methods such as milling, irradiation and extrusion are highly energy demanding and produce low grade cellulose. Also, the rates of known biological treatments are very low (11, 23-25).

Pretreatments that combine both chemical and physical processes are referred to as physicochemical processes (26). These methods are among the most effective and include the most promising processes for industrial applications. Hemicellulose hydrolysis is often nearly complete. As cellulose surface area increases, a decrease in cellulose degree of polymerization and crystallinity occurs. These changes greatly increase overall cellulose reactivity. Treatment rates are usually rapid (16-26). These pretreatment methods usually employ hydrolytic techniques using acids (hemicellulose hydrolysis) and alkalis for lignin removal (27-39).

The steam explosion process is well documented. Batch and continuous processes have been tested at laboratory and pilot scale by several research groups and companies (40-44). In steam explosion pretreatment, biomass is treated at high pressure, and high temperatures under acidic conditions i.e. 160° C. to 260° C. for 1 min to 20 min, at pH values<pH 4.0 (21, 17-23). The pressure of the pretreated biomass is suddenly reduced, which makes the materials undergo an explosive decompression leading to defibrization of the lignocellulosic fibers (45-47).

Steam explosion pretreatment is not very effective in dissolving lignin, but it does disrupt the lignin structure and increases the cellulose susceptibility to enzymatic hydrolysis. Steam explosion pretreatment generally results in extensive hemicellulose breakdown and, to a certain extent, to the degradation of xylose and glucose (40-44).

Steam explosion pretreatment has been successfully applied to a wide range of lignocellulosic biomasses. Acetic acid, sulfuric acid or sulfur dioxide are the most commonly used catalysts (40-44). Dilute acid- or sulfur dioxide-catalyzed steam explosion pretreatments refer to the use of 0.1-1.0% diluted sulfuric acid or 0.5-4.0% sulfur dioxide (45-47).

In acid catalyzed pretreatment processes catalysts must be recycled or the prehydrolysate stream obtained must be diluted in order to reduce the concentrations of toxic and inhibitory compounds to an acceptable level with respect to cellulolytic enzymes and fermenting organisms. As a result, large amounts of water are required prior to the enzymatic hydrolysis step. This results not only in increased capital equipment cost (tankage) but also in increased operating cost by limiting the final ethanol titer, due to the dilution factor applied to the stream of biomass prehydrolysate, which then dramatically increases energy requirements and cost of distillation (11, 20, 45-47).

In the autohydrolysis process, no added acid is required to reach pH values below 4.0. Acetic acid is released during the breakdown of acetylated hemicellulose resulting from the high pressure steam applied to the biomass during the cooking stage. The degree of hemicellulose acetylation is variable among different sources of biomass (11, 41, 48). The hemicellulose content of bagasse is high. Much of the hemicellulose is acetylated, which means the breakdown and solubilization of the hemicellulose, which occurs during pretreatment, leads to the formation of acetic acid.

The presence of acetic acid reduces the need for acid catalysts, which is beneficial to the pretreatment process and resulting downstream processing. However, acetic acid is a powerful inhibitor of both the hydrolysis and the glucose fermentation process. Acetic acid remains in the pretreated biomass and carries through to the hydrolysis and fermentation steps. A process is desired that includes a pretreatment step carried out at a pH values<pH 4.0 to maximize hemicellulose solubilization. However, after steam pretreatment, acetic acid and pre-treatment degradation products must be removed to enhance the digestibility of the cellulose in the enzymatic hydrolysis step and to enable a more rapid and complete conversion of glucose to ethanol in the fermentation step.

Pretreatment of lignocellulosic biomass is projected to be the single, most expensive processing step, representing about 20% of the total cost. Capital-intensiveness of lignocellulosic biomass pretreatment is a problem (49). Thus, a process is desired for efficient fractionation of lignocellulosic biomass into multiple streams that (i) contain value-added compounds and (ii) may significantly improve the overall economics of a biofuel production facility.

The growing commercial importance of xylo-oligosaccharides, non digestible sugar oligomers made up of xylose units, is based on their beneficial health properties; particularly the prebiotic activity and makes them good candidates as high value added bioproducts. Xylo-oligosaccharide mixtures from auto-hydrolysis of various agricultural residues exhibit a great prebiotic potential similar to commercially available xylo-oligosaccharide products (50-52).

As is apparent from the above discussion of known approaches, improving the overall ethanol yield and reducing enzyme usage or hydrolysis time are generally linked to increased operating costs. The increased costs may outweigh the value of the increased ethanol yield, rendering existing methods economically unacceptable.

SUMMARY OF THE INVENTION

It is now an object of the present invention to provide a process which overcomes at least one of the above disadvantages.

Compared to other biomass such as corncobs, the lower content of acetyl groups in bagasse, coupled with higher lignin content, make bagasse more difficult to pre-treat. For example, corncobs typically have acetyl groups in a concentration of about 4.6-5.5%, on a dry matter basis. Corncobs typically have a lignin content in the range of 4 to 7% on a dry matter basis. This is a lower lignin content than that of bagasse. Because of the concentration of acetyl groups and lignin, autohydrolysis can be achieved in corncobs without the addition of acid.

In contrast to corncobs, the concentration of acetyl groups in bagasse is typically in a range of about 3.2-3.5%, on a dry matter basis. Typically, bagasse has a lignin content of between 17 and 20%, which is up to five times the amount of lignin found in corncobs. Since bagasse has a lower content of acetyl groups and a higher content of lignin than that of corncobs, conventional processes to pretreat bagasse require the use of added mineral acid to assist with hydrolysis. However, the addition of mineral acid is disadvantageous as it catalyses the condensation of lignin which makes the cellulose less accessible to enzymatic hydrolysis.

The inventors have now surprisingly found that the use of an acid, such as mineral acid, as well as base can be completely avoided during pretreatment of bagasse by carefully selecting treatment conditions that result in autohydrolysis pre-treatment. This was surprising and unexpected in view of the relatively lower content of acetyl groups and higher content of lignin in bagasse. In particular, the inventors surprisingly discovered that by controlling the conditions of temperature, pressure and treatment time an efficient pretreatment of bagasse biomass can be achieved without the need for acid addition or base addition. The inventors have further discovered that the amount of acetic acid in the prehydrolysate obtained can be reduced by closely controlling the treatment conditions during the pretreatment step. In particular, the inventors have unexpectedly found conditions of temperature, pressure and treatment time at which sufficient acetic acid is produced to pretreat the bagasse biomass by the process of autohydrolysis, without the addition of acid or base, while at the same time limiting the acetic acid content in the prehydrolysate to a level which does not cause any significant delays in the downstream fermentation process.

The inventors have also discovered that the catalytic activities of cellulolytic enzymes are specifically inhibited by soluble forms of hemicellulose i.e. soluble xylo-oligosaccharides and xylose. Products of hemicellulose decomposition released during bagasse pretreatment which remain in the pretreated biomass, and carry through to the hydrolysis and fermentation steps, can negatively affect enzymatic conversion of cellulose to glucose.

Thus, a novel process is described for the continuous steam explosion pretreatment of bagasse wherein no acid, such as mineral acid, is added, and no base is added, and the amount of acetic acid released in the pretreatment step is controlled to maximize the efficiency of the steam exposure step. In a specific example, the bagasse is sugarcane bagasse. In another specific example, the bagasse is sorghum.

Further, and in addition to avoiding the use of acid or base during pretreatment, the extraction and/or washing steps herein also occurs without the addition of acid or base to minimize inhibitory disruption of downstream processes.

A sufficient residence time is provided to ensure proper breakdown/hydrolysis of the hemicellulose and activation of the cellulose fraction.

The steam explosion pretreated bagasse fibers are extracted under pressure prior to exiting the pretreatment reactor. Minimal water is used as an eluent to remove water soluble hemicellulose and cellulose degradation products such as, xylose, xylo-oligosaccharides, furans, fatty acids, sterols, ester, ethers and acetic acid. This extracting occurs without the addition of acid or base.

The inventors have discovered that complete removal of the inhibitory compounds is neither required nor desirable for the achievement of the most economically viable pretreatment process. The inventors have identified a narrow range of extraction conditions for the removal of inhibitory compounds in which hemicelluloses and hemicellulose hydrolysis and degradation products and other inhibitors are still present, but reduced to a level where they have a much reduced inhibitory effect on the enzymes. In addition, the fractionation of the biomass still provides an economical amount of valuable hemicellulose. The extraction is achieved with a lower volume of eluent and level of dilution making the process much more cost effective. Further, the extraction occurs without the addition of acid or base. In effect, the extraction cost is significantly less than the value of the increased ethanol yield, lower enzyme dosages, and the reduced processing times achieved. When combined with the ideal pretreatment temperature, time and purging of impurities, an economical process to convert bagasse to fermentable sugar is achieved.

A further important feature of our new process is the continual extraction of a liquid purge from the pretreatment process. This purge increases hemicellulose recovery by minimizing the formation of furfural from monomeric sugars released during pretreatment. The liquid purge from the pretreatment system is combined with the extracted hemicellulose. Extraction refers in general to a single or multiple step process of removing liquid portions from the fibers with or without addition or utilization of an eluent, (the diluting step) Typically the extraction is enhanced by use of a mechanical compressing device such as a modular screw device. The eluent can be recycled to increase the economy of its use or used for example in the known process of counter current washing as an example. The elution occurs without the addition of acid or base. Liquefied components in the steam treated lignocellulosic biomass and the dissolved components are subsequently removed from the fibrous solids. Generally this removes most of the dissolved compounds, the wash water, primarily consisting of hemicellulose hydrolysis and degradation products that are inhibitory to downstream hydrolysis and fermentation steps.

The extracting system in general uses a device that employs a mechanical pressing or other means to separate solids from liquid or air from solids. This can be accomplished under pressure as described above and/or under atmospheric pressure accomplished with several different types of machines that vary and the detail of which is not essential to this invention.

The extract stream containing the xylo-oligosaccharide fraction is combined with the liquid purge from the pretreatment system. The combined stream is collected and concentrated to the desired dryness for further applications. A final refining step is required for producing xylo-oligosaccharides with a degree of purity suitable for pharmaceuticals, food and feed, and agricultural applications. Vacuum evaporation can be applied in order to increase the concentration and simultaneously remove volatile compounds such as acetic acid and flavors or their precursors. Solvent extraction, adsorption and ion-exchange precipitation have been proposed by those skilled in the art.

A balance is preferably maintained between the removal of the water soluble components (xylo-oligosaccharide fraction) and the need to minimize the amount of washing/eluent water added. It is desirable to minimize water use, as the xylo-oligosaccharide fraction must be concentrated for its eventual use, which requires equipment and energy, both of which must be minimized.

As mentioned above, not only does pretreatment occur without the addition of acid or base, but the subsequent extraction step(s) also occurs without the addition of acid or base to minimize inhibitory disruption of downstream processes.

In addition, the economics of ethanol production demand the maximization of the value in all the byproduct streams from the process. As an example, acetic acid may be recovered for sale as an industrial chemical. Also, xylo-oligosaccharides, (non digestible sugar oligomers made up of xylose units), have beneficial health properties; particularly their prebiotic activity. This makes them good candidates as high value added bioproducts.

In the new process, pressurized activated cellulose is flashed into a cyclone by rapidly releasing the pressure to ensure an explosive decompression of the pretreated bagasse into fibrous solids and vapors. This opens up the fibers to increase accessibility for the enzymes. Purified cellulose with a low level of residual hemicellulose can be sent to the hydrolysis and fermentation stages.

In one aspect, the invention provides a continuous process for fractionation of bagasse biomass, comprising the steps of: a) subjecting the bagasse biomass to auto-hydrolysis treatment without the addition of acid or base by exposing the bagasse biomass to steam at a preselected temperature of between 170 and 220° C. and a preselected reaction pressure of between 100 and 322 psig, for a preselected exposure time of between 5 to 90 minutes, to remove a desired amount of a hemicellulose fraction from the bagasse biomass and activate a cellulose fraction of the bagasse biomass to obtain a pre-hydrolyzed bagasse biomass; and during the exposing step at the preselected temperature and reaction pressure i) continually purging liquid condensate and vapor formed to remove and collect a first liquid stream including water soluble compounds and a first vapor stream including volatile chemicals; b) selectively extracting at the preselected reaction pressure from the prehydrolysed bagasse biomass containing hemicellulose hydrolysis and degradation components, said extracting occurs without the addition of acid or base; c) rapidly releasing the preselected reaction pressure after the extracting step for explosive decompression of the pre-hydrolyzed bagasse into pretreated fibrous solids, vapor and condensate; and d) collecting the vapor and condensate from the explosive decompression for separation and recovery of byproducts.

In a specific example the bagasse is sugarcane bagasse. In another specific example, the bagasse is sorghum bagasse.

Preferably, the bagasse biomass has a moisture content of 50% to 70%, and is pre-heated to a temperature of about 100° C. for a minimum of about 10 minutes prior to pretreatment. The moisture of the bagasse biomass is adjusted without the addition of acid or base.

More preferably, the moisture content is 70%.

A further feature of this new process is the removal of toxic compounds prior to pretreatment by the addition of a mechanical squeezing step prior to pretreatment which improves fermentation by removing extractives found in the biomass. Preferably, the pre-heated bagasse is squeezed from atmospheric pressure to a selected pressure required for pre-treatment while removing a stream of extractives. Said removal of toxic compounds occurs without the addition of acid or base.

Preferably, the liquid from the pretreatment purge stream is blended with the liquid extracted from the prehydrolysed bagasse biomass.

Preferably, the preselected exposure time and preselected temperature are selected to achieve a severity index of 3.88 to 4.11. More preferably, the severity index is 4.0. Preferably, the preselected temperature is between 190 and 210° C., the preselected pressure is between 165 and 260 psig, and the preselected exposure time is between 7 and 10 minutes. More preferably, the preselected temperature is about 205° C., the preselected pressure is about 235 psig and the preselected exposure time is about 8 minutes.

Preferably, the bagasse biomass is washed and subsequently separated from the dissolved hemicellulose and lignin free xylo-oligosaccharides and remaining inhibitory chemicals prior to explosive decompression. Said washing occurs without the addition of acid or base.

Preferably, the bagasse biomass is washed under a steam pressure that ranges from 100 psig to 290 psig prior to the step of explosive decompression. Preferably, the pretreated fibrous solids are washed with water. Said washing occurs without the addition of acid or base.

Preferably, the washed fibrous solids are separated from the wash water by a separation process selected from the group consisting of compressing, filtering, centrifuging, and combinations thereof. Preferably, the washing is counter current washing. The wash water is preferably recycled wash water. Said separation process occurs without the addition of acid or base.

BRIEF DESCRIPTION OF THE DRAWINGS

Other objects and advantages of the invention will become apparent upon reading the detailed description and upon referring to the drawings in which.

Table 1 shows cellulose to glucose conversion times of 12% consistency bagasse hydrolysate at various levels of digestion versus severity index for bagasse biomass.

Hydrolysis was carried out at 50° C., pH 5.0 and 0.4% enzyme load.

Pre-treatment of bagasse was carried out at pilot scale (500 kg per day). 250 liter hydrolysis of bagasse pre-hydrolysate was carried out at 12% consistency, 50° C., pH 5.0 and 0.4% enzyme load. Fermentation of bagasse hydrolysate was carried out at 33° C., pH 5.3 using an industrial grade C6-fermenting yeast.

Hydrolysis and fermentation pH adjustment was carried out using liquid ammonia (30%). Grey circles indicate glucose concentration. Black squares indicate ethanol concentration.

DETAILED DESCRIPTION OF THE PREFERRED EMBODIMENTS

Before explaining the present invention in detail, it is to be understood that the invention is not limited to the preferred embodiments contained herein. The invention is capable of other embodiments and of being practiced or carried out in a variety of ways. It is to be understood that the phraseology and terminology employed herein are for the purpose of description and not of limitation.

The abbreviations used in the figures have the following meaning:
° C., temperature in degree Celsius
ms, millisecond
DM, Dry matter
SI, Severity index Pre-Treatment of Sugarcane Bagasse This invention is a new process for fractionating lignocellulosic biomass from bagasse into two main components, specifically a cellulose-rich corncob fibre and a xylo-oligosaccharides-rich solution. The cellulose-rich component is valuable for many purposes. Specifically it may be more easily hydrolyzed to glucose which in turn may be more easily fermented to ethanol or other biofuels than in previous processes. In a specific example, the bagasse is sugarcane bagasse. In another specific example, the bagasse is sorghum bagasse.

A preferred aspect of the invention is a continuous process for the pretreatment of bagasse that generates highly reactive cellulose prehydrolysate with a reduced content of compounds which have an inhibiting effect on cellulose hydrolysis and glucose fermentation. Not only does pretreatment occur without the addition of acid or base, but the subsequent extraction step(s) also occurs without the addition of acid or base to minimize inhibitory disruption of downstream processes.

Another preferred aspect of the invention is a process for the pretreatment of bagasse, for generating a lignin free solution of xylo-oligosaccharides with a ratio of xylo-oligosaccharide to acetic acid and volatile compounds from hemicellulose degradation of greater than 4.

The preferred process of the invention includes the steps of pre-steaming ground, preheated bagasse fibers to add moisture and remove air. Pre-steaming occurs without the addition of base or acid. This is followed by a pressurized squeezing step that removes a certain quantity of toxic extractives. Next the pre-steamed, squeezed biomass is pretreated at 170° C. to 220° C. at 100 to 322 psig for 5 to 90 minutes without the use of mineral acid catalysts. The pretreatment preferably includes the continuous purging of volatile and liquid compounds. The exposing step preferably steam treats the biomass to a temperature and hold time for a Severity Index of 3.8 SI to 4.1, the Severity Index being calculated according to the equation:

$$\text{Severity Index} = \text{Log} \times \text{Exp}(\text{Temperature }°\text{C.} - 100)/14.75) \times \text{Retention Time (min)}.$$

The exposing step most preferably has a severity index of 4.0.

The exposing of bagasse to a severity index of 4.0 leads to a final pH of 3.5 to 4.0.

The pretreatment step occurs without the addition of acid or base.

The process also includes extraction of the steam treated fibers with/or without eluent addition under pressure to remove water soluble hemicelluloses, acids and hemicellulose and cellulose degradation products. As an option these inhibitors may be extracted after pretreatment or both during and after. The extraction of the soluble biomass from the fiber preferably results in 4% to 10% xylose based sugars consisting of monomers and oligosaccharides remaining in the pre-hydrolysis fibers.

The extraction occurs without the addition of acid or base.

The hemicellulose rich extract is combined with the liquid purge from pretreatment that contains an additional amount of hemicellulose extracted under pressure.

The extracted fibers, also referred to as prehydrolysate, are separated from the gaseous reaction products in a cyclone separator, collected at the bottom of the separator, then shredded and diluted to the desired consistency and subsequently transported to the enzymatic hydrolysis step.

The prehydrolysate is diluted with water to 10-30% consistency and then reacted with cellulase enzymes to produce glucose. The glucose rich solution is readily utilized in the subsequent fermentation step where an organism converts the glucose into ethanol.

EXAMPLE

Figure 1:
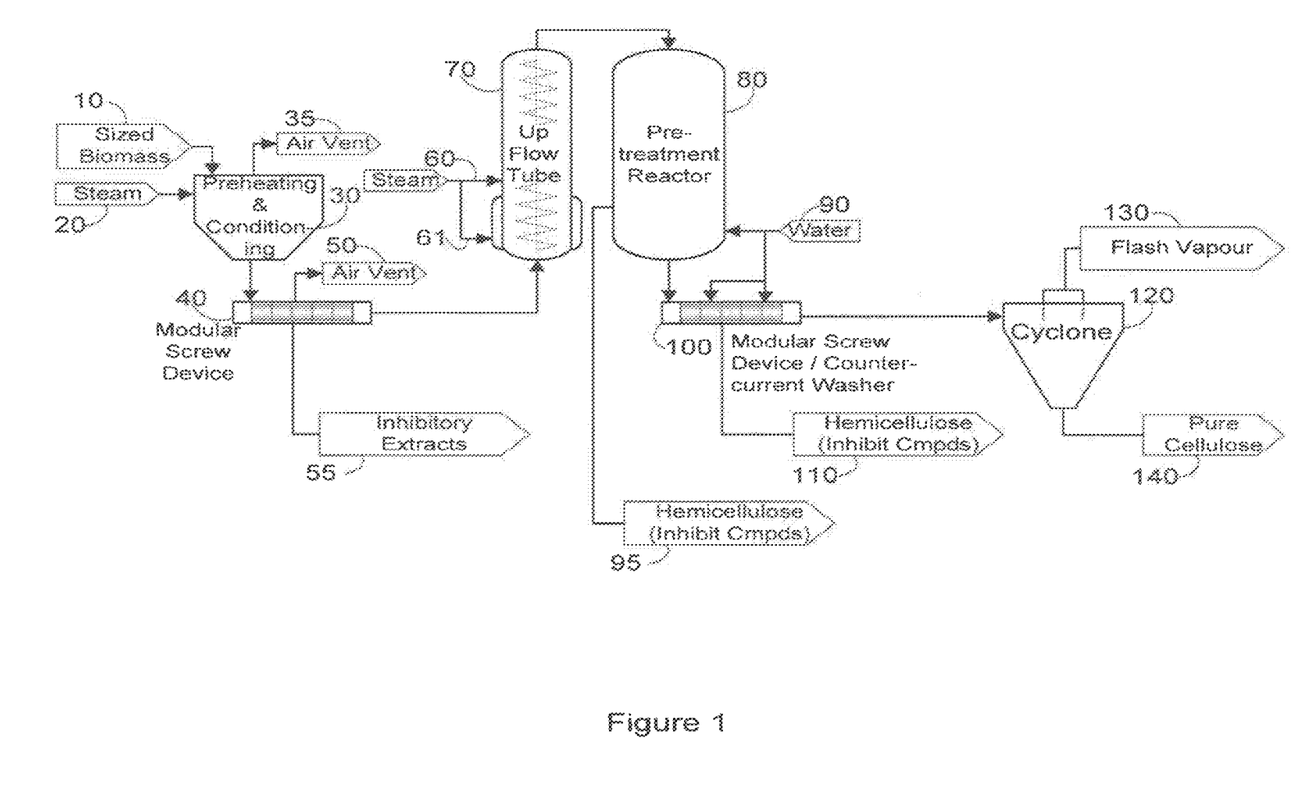
FIG. 1 shows a process diagram of the continuous pre-treatment unit proposed in the example.

In the following example, reference numbers refer to features of the pre-treatment system and process streams, as shown in FIG. 1.

Continuous steam explosion pretreatment of bagasse is carried out in a continuous steam gun explosion pretreatment system (FIG. 1).

50% to 70% moisture bagasse fibers (10) are received and fed through a V shaped hopper and screw auger (not shown) using a feed rate of 40 kg bagasse fibers per hour on a dry matter basis.

Bagasse fibers are preheated with live steam (20) at atmospheric pressure, in a holding bin or pre-heating and conditioning container (30) to a temperature of 95-100° C. for about 10-60 min. Moisture content is adjusted to 75-80%. This pre-heating and moisture content adjustment occurs without the addition of acid or base. Air and steam are vented through an air vent (35) from the pre-heating and conditioning container (30).

Preheated bagasse fibers are compressed in a first modular screw device (40) to remove air (50) through an air vent and inhibitory extracts (55). The bagasse fibers are then fed into a pressurized upflow tube (70).

Pressurized saturated steam at temperatures of 205° C. is injected upstream of and/or into the up flow tube (70) by direct injection (60) and/or indirect injection of steam (61) in a jacketed section of the up flow tube until the desired cooking pressure is reached.

Bagasse fibers are moved through the up flow tube with the aid of a screw conveyor/mixer (3 min) and are discharged into the pretreatment reactor (80).

Bagasse fibers are continuously discharged from the pretreatment reactor to a second pressurized modular screw device (100) after a residence time of 5 min at 205° C. in the pretreatment reactor (80). Pretreatment occurs without the addition of acid or base.

During the residence time, condensate and cooking liquids collected at the bottom of the pre-treatment reactor are purged through purge discharge control valve (95).

Pretreated bagasse fibers are washed with water under pretreatment pressure. Hot water (90) is added to dilute the pretreated bagasse as the fibers are discharged from the pretreatment reactor. Further hot water is also added along the pressing device (100) to reach a ratio of about 6:1 wash water to bagasse and achieve a greater extraction of hemicellulose. This washing and addition of hot water occurs without the addition of acid or base. The extracted hemicellulose solution (110) is collected, combined with the hemicellulose stream from the liquid purge and concentrated to the desired dryness for further applications.

The pressurized washed bagasse fibers are flashed into a cyclone (120). The solids i.e. purified cellulose collected at the bottom of cyclone separator are subjected to further processing i.e. shredded and then diluted with fresh water to the desired consistency for hydrolysis and fermentation. This processing occurs without the addition of acid or base.

The gaseous components are collected, condensed (130) and fed to the condensate tank. Any gaseous emissions from the steam gun, the cyclone separator and other parts of the setup are collected and treated in an environmental control unit (not shown). Cleaned gases are exhausted to atmosphere from the environmental control unit.

Screening of bagasse pre-treatment optima was carried out at pilot scale using 0.4% load of a commercial mixture of cellulase and hemicellulase enzymes on a dry matter basis.

Pre-treatment of bagasse fibers carried out with a severity index of 4.0 SI led to the production of the most digestible bagasse pre-hydrolysates. Severity of 4.0 let to the shortest times to reach 50% to 90% of the maximum theoretical cellulose to glucose conversion (See Table 1).

Extracted cellulose from continuous pilot scale pre-treatment was highly susceptible to enzymatic hydrolysis. 80% of the maximum theoretical cellulose to glucose conversion was achieved in 111 hours using only 0.3% load of commercial enzyme product (Table 1).

Figure 2:
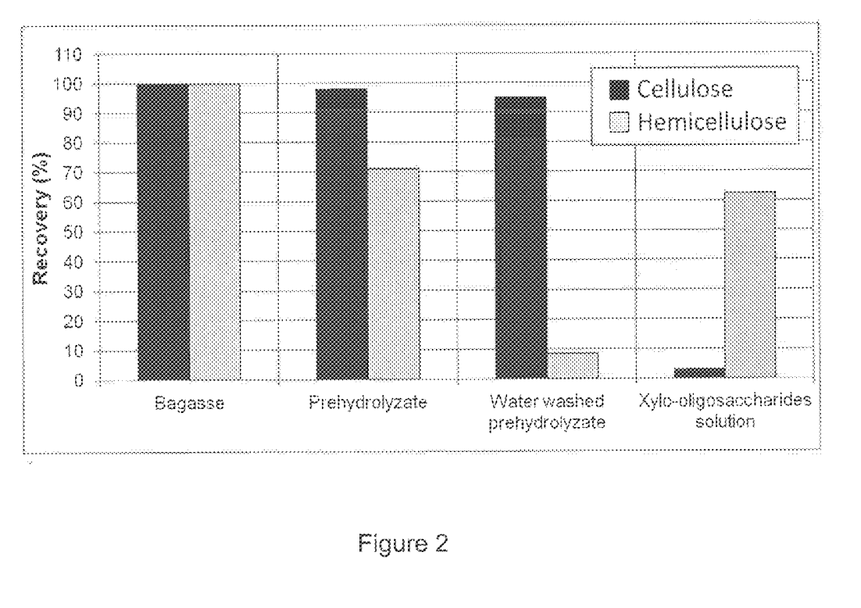
FIG. 2 shows the total percentage recovery of cellulose and hemicellulose produced over the fractionation of bagasse.

Cellulose extraction from bagasse was carried out at pilot scale with a percentage recovery of 98% (FIG. 2). The content of inhibitory compounds in the extracted cellulose was less than 1% (w/w, DM) acetic acid and no furans were detected prior to or following enzymatic hydrolysis and fermentation.

The target molecules were sugar monomers such as glucose and xylose as well ethanol, toxic compounds such as different carboxylic acids, namely acetic acid, succinic acid and lactic acid and degradation products of carbohydrates such as HMF and furfural. Concentration of fermentation by product such as glycerol is also measured.

Elemental analysis and wet chemistry analysis of samples (lignin, protein, fat, ash, Non fiber carbohydrate) was carried out by an external laboratory (DairyOne). Internal controls i.e. samples with known composition and duplicate samples are included in set of samples sent for analysis.

Carbohydrate composition analysis of samples was carried out using a modified TAPPI method T249 and a GC 7890A from Agilent equipped with a column DB225 from Agilent. Briefly, the method is modified beginning with the alkination step. Instead of using barium hydroxide (as required by the TAPPI method), ammonium hydroxide is used. The acetylation step is altered by using a catalyst (1-methyl imidazole) and a larger volume of acetic anhydride than is required by the TAPPI method T249.

TABLE 1

| Conversion Time (hours) | Severity Index (SI) | 3.35* | 3.55** | 3.64 | 3.79 | 3.85 | 3.99 | 4.08 | 4.29 | 4.56 |
|---|---|---|---|---|---|---|---|---|---|---|
| | Temperature (° C.) | 190 | 190 | 200 | 205 | 200 | 205 | 215 | 215 | 215 |
| | Time (min) | 5 | 8 | 5 | 5 | 8 | 8 | 5 | 8 | 15 |
| Conversion (%) | 50 | >200 | >200 | 56 | 35 | 30 | 25 | 32 | 38 | 48 |
| | 60 | >200 | >200 | 110 | 62 | 52 | 44 | 55 | 58 | 61 |
| | 70 | >200 | >200 | >200 | 118 | 84 | 66 | 88 | 84 | 90 |
| | 80 | >200 | >200 | >200 | >200 | 178 | 111 | 126 | 140 | 157 |
| | 90 | >200 | >200 | >200 | >200 | >200 | 200 | >200 | >200 | >200 |

*20% conversion were reached in 100 hours
**30% conversion were reached in 100 hours 63% of the incoming hemicellulose was recovered in a soluble form in the lignin free xylo-oligosaccharides solution consisting of a blend of the purge from the pretreatment step and the hemicellulose rich stream from the extraction stage. (FIG. 2). 85% of the hemicellulose sugars were recovered in an oligomeric form.

Figure 3:
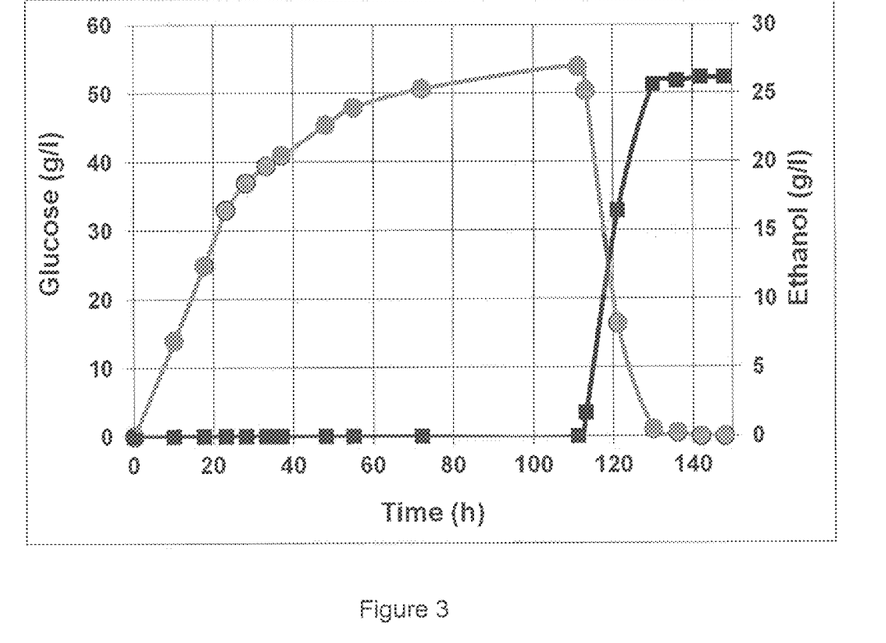
FIG. 3 illustrates the susceptibility of pre-treated cellulose from bagasse to enzymatic hydrolysis (cellulose to glucose conversion) and fermentability of hydrolyzed cellulose (glucose to ethanol conversion).

Samples of the continuously pre-treated bagasse were hydrolyzed and fermented in a 250 liter fed batch hydrolysis and fermentation trial (FIG. 3). The results were in accordance with laboratory scale results (Table 1). A concentration of 54 g/L glucose was reached when 80% of the maximum theoretical cellulose to glucose conversion was achieved i.e. 110 hours hydrolysis of 13% consistency slurry, using only 0.3% dm load of commercial cellulases product.

The fermentability of the hydrolyzed cellulose was high. A concentration of 2.6% (w/v) alcohol was reached in 20 hours (FIG. 3). This is equivalent to a glucose to ethanol conversion yield of 95%.

Samples of biomass were analyzed at each step of the process using the following analytical methods:

Dry matter: DM determination was carried out by incubating solid (1 g to 2 g) and liquid (5 g to 10 g) samples at 130° C. for a period of 16 h to 24 h.

HPLC analysis: Quantification of soluble products in liquid samples and slurry was carried out by High Performance Liquid Chromatography analysis (HPLC). The HPLC system used was an AGILENT 1200 Series equipped with a cation exchange column HPX 87H from BioRad, a refractive index detector and an isocratic pump. Samples i.e. liquid, slurry and solid in suspension were centrifuged, filtered and diluted using 0.02 N sulfuric acid also used as eluent.

REFERENCES (1) Shapouri H et al. (1995) USDA Report 721. Estimating the net energy balance of corn ethanol.
(2) Shapouri H et al. (2002) USDA Report 813. The Energy Balance of corn ethanol: an update.
(3) Chow J et al. (2003) Science, 302, 1528-1531 Energy resources and global development.
(4) Wald M L, Barrionuevo A (2007) New York Times, April 7th, The Energy challenge: A Renewed push for ethanol, without the corn.
(5) Greeg D (2008) Biocycle, 49, 11-47. Commercializing cellulosic ethanol.
(6) Hill J et al. (2006) Proc. Natl. Acad. Sci. USA, 103, 11206-11210. Environmental, economic, and energetic costs and benefits of biodiesel and ethanol biofuels.
(7) Farrell A E et al. (2006) Science, 311, 506-508. Ethanol can contribute to energy and environmental goals.
(8) Somerville C (2007) Current biology, 17, 115-119. Biofuels.
(9) Schuetzle D et al. (2007) Western Governors' Association. Alcohol fuels from biomass-Assessment of production technologies.
(10) Chum L, Overend R (2002) Fuel Processing technology, 71, 187-195. Biomass and renewable fuels.
(11) Wyman C E (1996) Taylor & Francis: Washington D.C., USA, Handbook on bioethanol: production and utilization.
(12) Delmer D P, Amor Y (1995) Plant Cell, 7, 987-1000. Cellulose biosynthesis.
(13) Morohoshi N (1991) In Wood and cellulosic chemistry; Hon, D. N. S, Shiraishi, N., Eds.; Marcel Dekker, Inc.: New York, USA, Chemical characterization of wood and its components.

(14) Ha M A et al. (1998) Plant J. 1998, 16, 183-190. Fine structure in cellulose microfibrils: NMR evidence from onion and quince.
(15) Palmqvist E, Hahn-Hägerdal B (2000) Bioresource Technol., 74, 25-33. Fermentation of lignocellulosic hydrolysates. II: Inhibitors and mechanisms of inhibition.
(16) De Vrije T et al (2002) International journal of hydrogen energy, 27, 1381-1390. Pretreatment of *miscanthus* for hydrolgen production by *thermotoga elfii*.
(17) Galbe M, Zacchi G (2002) Appl Microbiol Biotechnol 59 618-628. A review of the production of ethanol from softwood.
(18) Torget R et al. (1991) Bioresource Technol., 35, 239-246. Dilute sulfuric acid pretreatment of hardwood bark.
(19) Donghai S et al. (2006) Chinese J. Chem. Eng., 14, 796-801. Effects of different pretreatment modes on the enzymatic digestibility of corn leaf and corn stalk.
(20) Sun Y, Cheng J (2002) Bioresources Technol., 83, 1-11. Hydrolysis of lignocellulosic materials for ethanol production: A review.
(21) McMillan J D (1994) In Enzymatic Conversion of Biomass for Fuels Production; Himmel, M. E., Baker, J. O., Overend, R. P., Eds.; ACS: Washington D.C., USA, 1994; pp. 292-324. Pretreatment of lignocellulosic biomass.
(22) Fan L et al (1982) Adv. Biochem. Eng. Biotechnol., 23, 158-183. The nature of lignocellulosics and their pretreatments for enzymatic hydrolysis.
(23) Mosier N et al. (2005) Bioresources Technol, 96, 673-686. Features of promising technologies for pretreatment of lignocellulosic biomass.
(24) Henley R G et al. (1980) Enzyme Microb. Tech., 2, 206-208. Enzymatic saccharification of cellulose in membrane reactors.
(25) Berlin A et al. (2006) J. Biotechnol., 125, 198-209. Inhibition of cellulase, xylanase and beta-glucosidase activities by softwood lignin preparations.
(26) Chandra R et al. (2007) Adv. Biochem. Eng. Biotechnol, 108, 67-93. Substrate pretreatment: The key to effective enzymatic hydrolysis of lignocellulosics?
(27) Kassim E A, EI-Shahed A S (1986) Agr. Wastes, 17, 229-233. Enzymatic and chemical hydrolysis of certain cellulosic materials.
(28) Xu Z et al (2007) Biomass Bioenerg. 2007, 31, 162-167. Enzymatic hydrolysis of pretreated soybean straw.
(29) Vaccarino C et al (1987) Biol. Waste, 20, 79-88. Effect of SO2NaOH and Na2CO3 pretreatments on the degradability and cellulase digestibility of grape marc.
(30) Silverstein R A et al (2007) Bioresource Technol., 2007, 98, 3000-3011. A comparison of chemical pretreatment methods for improving saccharification of cotton stalks.
(31) Zhao X et al (2007) Bioresource Technol., 99, 3729-3736. Comparative study on chemical pretreatment methods for improving enzymatic digestibility of crofton weed stem.
(32) Gaspar M et al (2007) Process Biochem., 2007, 42, 1135-1139. Corn fiber as a raw material for hemicellulose and ethanol production.
(33) Saha B C, Cotta M A (2006) Biotechnol. Progr., 22, 449-453. Ethanol production from alkaline peroxide pretreated enzymatically saccharified wheat straw.
(34) Saha B C, Cotta M A (2007) Enzyme Microb. Tech., 41, 528-532. Enzymatic saccharification and fermentation of alkaline peroxide pretreated rice hulls to ethanol.
(35) Mishima D et al (2006) Bioresource Technol. 2006, 97, 2166-2172. Comparative study on chemical pretreatments to accelerate enzymatic hydrolysis of aquatic macrophyte biomass used in water purification processes.
(36) Sun X F et al (2005) Carbohyd. Res., 340, 97-106. Characteristics of degraded cellulose obtained from steam-exploded wheat straw.
(37) Alizadeh H et al (2005) Appl. Biochem. Biotechnol., 124, 1133-41. Pretreatment of switchgrass by ammonia fiber explosion (AFEX).
(38) Chundawat S P et al (2007) Biotechnol. Bioeng., 96, 219-231. Effect of particle size based separation of milled corn stover on AFEX pretreatment and enzymatic digestibility.
(39) Eggeman T, Elander R T. (2005) Bioresource Technol., 96, 2019-2025. Process and economic analysis of pretreatment technologies.
(40) Chum H L (1985) Solar Energy Research Institute: Golden, Colo., 1-64. Evaluation of pretreatments of biomass for enzymatic hydrolysis of cellulose.
(41) Taherzadeh M J, Karimi K (2007) Bioressources, 2, 472-499. Process for ethanol from lignocellulosic materials I: Acid-based hydrolysis processes.
(42) Ruiz E et al (2008) Enzyme Microb. Tech., 42, 160-166. Evaluation of steam explosion pretreatment for enzymatic hydrolysis of sunflower stalks.
(43) Ballesteros M et al. (2004) Process Biochem., 39, 1843-1848. Ethanol from lignocellulosic materials by a simultaneous saccharification and fermentation process (SFS) with *Kluyveromyces marxianus* CECT 10875.
(44) Negro M J et al (2003) Appl. Biochem. Biotechnol., 105, 87-100. Hydrothermal pretreatment conditions to enhance ethanol production from poplar biomass.
(45) Kurabi A et al (2005) Appl. Biochem. Biotechnol., 121-124. Enzymatic hydrolysis of steam exploded and ethanol organosolv-pretreated Douglas-firby novel and commercial fungal cellulases.
(46) Varga E et al (2004) Appl. Biochem. Biotechnol., 509-523. Optimization of steam pretreatment of corn stover to enhance enzymatic digestibility.
(47) Eklund R (1995) Bioresource Technol., 52, 225-229. The influence of SO2 and H2SO4 impregnation of willow prior to steam pretreatment.
(48) Yang B, Wyman C E (2004) Biotechnol. Bioeng, 86, 88-95. Effect of xylan and lignin removal by batch and flowthrough pretreatment on the enzymatic digestibility of corn stover cellulose.
(49) Eggeman T, Elander R T. (2005) Bioresource Technol., 96, 2019-2025. Process and economic analysis of pretreatment technologies.
(50) Nabarlatz D, et al (2007) Carbohydrate Polymers, 69, 20-28. Autohydrolysis of agricultural by-products for the production of xylo-oligosaccharides.
(51) Vazquez M, et al (2006) Industrial Crops and Products, 24, 152-159. Enhancing the potential of oligosaccharides from corncob autohydrolysis as prebiotic food ingredients.
(52) Moura P, et al (2007) LWT, 40, 963-972. IN vitro fermentation of xylooligosaccharides from corncobs autohydrolysis by *Bifidobacterium* and *Lactobacillus* strains.

What is claimed is:
1. A continuous process for fractionation of a bagasse biomass, consisting of the steps of:
   a) subjecting the biomass to auto-hydrolysis treatment without the addition of acid or base to obtain a prehydrolyzed bagasse biomass by exposing the biomass to steam in a reaction vessel at a preselected temperature of between 170 and 220° C. and a preselected reaction pressure of between 100 and 322 psig, for a preselected exposure time of between 5 to 90 minutes, to remove a desired amount of a hemicellulose fraction from the bagasse biomass and activate a cellulose fraction of the bagasse biomass; and subjecting the biomass to auto-hydrolysis treatment without the addition of acid to obtain a pre-hydrolyzed bagasse biomass during the exposing step at the preselected temperature and reaction pressure continually purging liquid condensate and vapor formed during the exposure step to remove and collect a first liquid stream containing water soluble compounds and a first vapor stream containing volatile chemicals;

b) selectively extracting at the selected reaction pressure from the prehydrolysed bagasse biomass a second liquid stream containing hemicellulose hydrolysis and degradation components as a hemicellulose degradation stream, said extracting occurring without the addition of acid or base;

c) rapidly releasing the preselected reaction pressure after the extracting step for explosive decompression of the pre-hydrolyzed bagasse into pretreated fibrous solids, vapor and condensate;

d) collecting the vapor and condensate from the explosive decompression for separation and recovery of byproducts;

e) optionally the bagasse biomass is adjusted to a moisture content of 50% to 70%, and is pre-heated to a temperature of about 100° C. for a minimum of about 10 minutes prior to pretreatment, wherein the adjustment of moisture content occurs without the addition of acid or base, f) optionally the pre-heated bagasse biomass is compressed prior to the exposure step to the selected pressure required for the exposure step for removing a third liquid stream containing extractives, q) optionally the first liquid stream from the pretreatment purge is blended with the second liquid stream extracted from the prehydrolysed bagasse biomass, h) optionally the bagasse biomass is washed and subsequently separated from dissolved hemicellulose and lignin free xylo-oligosaccharides and remaining inhibitory chemicals prior to the explosive decompression, wherein said washing occurs without the addition of acid or base, i) optionally pretreated fibrous solids are washed with water, wherein said washing occurs without the addition of acid or base, and j) optionally the washed fibrous solids are separated from the wash water by a separation process selected from the group consisting of compressing, filtering, centrifuging, and combinations thereof.

2. The process of claim 1, wherein the bagasse biomass is adjusted to a moisture content of 50% to 70%, and is pre-heated to a temperature of about 100° C. for a minimum of about 10 minutes prior to pretreatment, wherein the adjustment of moisture content occurs without the addition of acid or base.

3. The process of claim 2, wherein the moisture content is 80%.

4. The process of claim 2, wherein the pre-heated bagasse biomass is compressed prior to the exposure step to the selected pressure required for the exposure step for removing a third liquid stream containing extractives.

5. The process of claim 1, wherein the first liquid stream from the pretreatment purge is blended with the second liquid stream extracted from the prehydrolysed bagasse biomass.

6. The process of claim 1, wherein preselected exposure time and preselected temperature are selected to achieve a severity index of 3.88 to 4.11.

7. The process of claim 6, wherein the severity index is 4.0.

8. The process of claim 1, wherein the preselected temperature is between 190 and 210° C., the preselected pressure is between 165 and 260 psig, and the preselected exposure time is between 7 and 10 minutes.

9. The process of claim 8, wherein the preselected temperature is about 205° C., the preselected pressure is about 235 psig and the preselected exposure time is about 8 minutes.

10. The process of claim 1, wherein the bagasse biomass is washed and subsequently separated from dissolved hemicellulose and lignin free xylo-oligosaccharides and remaining inhibitory chemicals prior to the explosive decompression, wherein said washing occurs without the addition of acid or base.

11. The process of claim 10, wherein the bagasse biomass is washed under a steam pressure that ranges from 100 psig to 290 psig prior to the explosive decompression, wherein said washing occurs without the addition of acid or base.

12. The process of claim 1, wherein pretreated fibrous solids are washed with water, wherein said washing occurs without the addition of acid or base.

13. The process of claim 12, wherein the washed fibrous solids are separated from the wash water by a separation process selected from the group consisting of compressing, filtering, centrifuging, and combinations thereof.

14. The process of claim 13, wherein the washing is counter current washing.

15. The process of claim 12, wherein the wash water is recycled wash water.

16. The process of claim 1, wherein said bagasse is sugarcane bagasse.

17. The process of claim 1, wherein said bagasse is sorghum bagasse.

* * * * *